United States Patent
Dejean et al.

(10) Patent No.: US 9,545,979 B2
(45) Date of Patent: Jan. 17, 2017

(54) FLOATING VESSEL FOR COLLECTING LIQUID SAMPLES

(71) Applicant: SPYGEN, Le Bourget du Lac (FR)

(72) Inventors: Tony Dejean, Viviers du Lac (FR); Olivier Le Meaux, Lyons (FR)

(73) Assignee: SPYGEN (FR)

( * ) Notice: Subject to any disclaimer, the term of this patent is extended or adjusted under 35 U.S.C. 154(b) by 0 days.

(21) Appl. No.: 14/646,728

(22) PCT Filed: Nov. 22, 2013

(86) PCT No.: PCT/FR2013/052835
§ 371 (c)(1),
(2) Date: May 21, 2015

(87) PCT Pub. No.: WO2014/080143
PCT Pub. Date: May 30, 2014

(65) Prior Publication Data
US 2015/0336640 A1    Nov. 26, 2015

(30) Foreign Application Priority Data

Nov. 23, 2012  (FR) ..................... 12 61183

(51) Int. Cl.
| | |
|---|---|
| *B63B 3/08* | (2006.01) |
| *B63B 35/71* | (2006.01) |
| *B63H 7/02* | (2006.01) |
| *B63H 7/00* | (2006.01) |
| *B63B 35/00* | (2006.01) |
| *G01N 1/12* | (2006.01) |
| *G01N 1/10* | (2006.01) |

(52) U.S. Cl.
CPC ................ *B63B 3/08* (2013.01); *B63B 35/00* (2013.01); *B63B 35/71* (2013.01); *B63H 7/00* (2013.01); *B63H 7/02* (2013.01); *G01N 1/12* (2013.01); *B63B 2035/006* (2013.01); *B63B 2231/00* (2013.01); *G01N 2001/1031* (2013.01)

(58) Field of Classification Search
CPC .......... B63B 35/00; B63B 35/71; B63H 7/00; B63H 7/02
USPC ...................................... 440/6, 37; 114/56.1
See application file for complete search history.

(56) References Cited

U.S. PATENT DOCUMENTS

| | | |
|---|---|---|
| 5,218,918 A | 6/1993 | Cline |
| 6,536,272 B1 | 3/2003 | Houston et al. |

FOREIGN PATENT DOCUMENTS

DE    1251176 B    9/1967

OTHER PUBLICATIONS

Written Opinion issued Jan. 14, 2014 re: Application No. PCT/FR2013/052835; citing: U.S. Pat. No. 6,536,272 B1.

(Continued)

*Primary Examiner* — Lars A Olson
(74) *Attorney, Agent, or Firm* — Cantor Colburn LLP

(57) ABSTRACT

The invention relates to a floating vessel for taking liquid samples, comprising a shell (2) that has a hull (3) to be submerged in a liquid medium below the water line and a superstructure (4) arranged above the water line; the vessel also comprises air propulsion means, means for taking and storing samples, and means for remotely controlling the air propulsion means and the sampling means; and the vessel further comprises a secondary detachable shell (32) provided with means for fixing to the shell (2) of the vessel, covering at least the hull of the vessel.

13 Claims, 4 Drawing Sheets

(56) References Cited

OTHER PUBLICATIONS

International Search Report issued Jan. 14, 2014 re: Application No. PCT/FR2013/052835; citing: U.S. Pat. No. 6,536,272 B1, U.S. Pat. No. 5,218,918 A and DE 12 51 176 B.

FLOATING VESSEL FOR COLLECTING LIQUID SAMPLES

TECHNICAL FIELD

The present invention relates to an aquatic vessel for collecting samples.

BACKGROUND

In the field of biological or chemical research, it is useful to perform collections in aquatic environments in order to later on, perform, DNA analyses for example.

During a collection, it is quite critical to not disturb and contaminate the environment in which the collection is performed. It is understood that contaminated collected samples have no scientific value.

It is known for example, from document U.S. Pat. No. 6,536,272, a vessel having means for collecting liquid samples.

However, the current collection means, such as for example the vessel shown in document U.S. Pat. No. 6,536,272, do not ensure that the collection vessel itself does not contaminate the environment in which the collection is performed.

In this technical context, there is hence a need for an aquatic vessel which allows performing collections without contaminating the environment.

BRIEF SUMMARY

The present invention relates to a floating vessel for collecting liquid samples comprising a hull having a canoe body intended to be immersed in a liquid environment below a waterline and a superstructure located above the waterline, the vessel comprising aerial propulsion means and means for collecting and storing samples and remote control means of the aerial propulsion means and collection means, characterized in that the vessel comprises a removable secondary hull fitted with means for fixing on the hull of the vessel covering at least the canoe body of the vessel.

Hence, the invention provides a standalone vessel which is capable of being displaced on a water plane or on a water course in order to perform collections, on which a secondary hull is placed at each new collection campaign. In other words, the invention provides a vessel which guarantees the absence of any contamination of the environment in which the collections are to be performed.

According to several features of the invention which may be implemented independently or in combination:
  the hull has a peripheral rib and in that the secondary hull has a peripheral fold-back designed to snap-fit over the rib of the hull.
  the vessel comprises a peristaltic pump comprising a roller assembly pressing an elastic tube located outside the hull.
  the superstructure has a removable cowl wherein there is arranged at least one cell designed to receive a container wherein a collected sample may be stored.
  the cowl comprises a transparent bubble located above a cell.
  the vessel comprises at least one camera motorized with respect to at least one vertical axis Z of the vessel.
  the camera is positioned in line with the transparent bubble.
  the hull has, at its stem, a transparent panel.
  the camera is movable and is motorized about a transverse axis Y of the vessel so as to pivot from a position where the camera is positioned facing the transparent bubble and a position where the camera is positioned facing the transparent panel.
  the secondary hull is made of a transparent material.
  the vessel comprises at least one propeller positioned at the end of a mast projecting from the superstructure of the vessel, the propeller being driven by an electric motor placed at the top of the mast.
  the vessel comprises two masts connected to each other by a drive belt allowing to synchronize the orientation of the propellers.
  the vessel embeds one or several batteries powering the motors driving at least one of the equipment of the set comprising the pump, the camera(s), the propeller(s).

BRIEF DESCRIPTION OF THE DRAWINGS

For a good understanding, the invention is described with reference to the accompanying figures representing, by way of non-limiting example, an embodiment of an aquatic vessel according to the latter.

DETAILED DESCRIPTION

Figure 1:
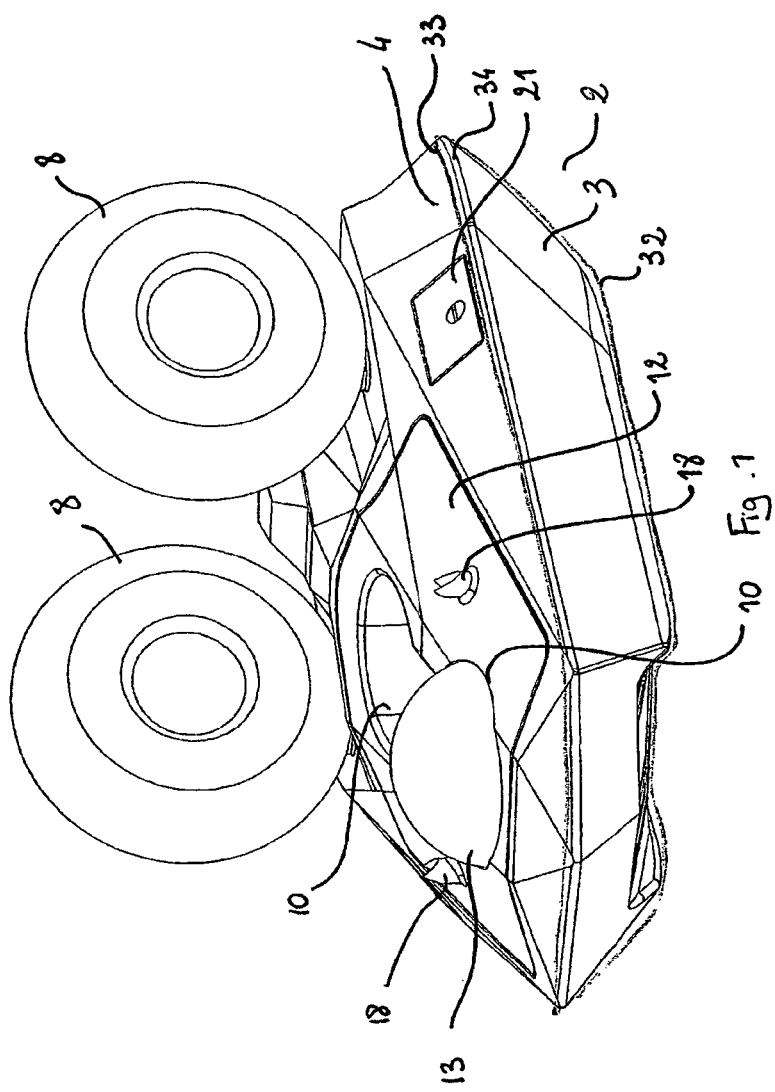
FIG. 1 is a three-quarter front perspective view of the aquatic vessel according to the invention.

Referring first to FIG. 1, the aquatic vessel according to the invention has, in its illustrated embodiment, a generally trapezoidal shape. The vessel comprises a hull 2 of which a portion called canoe body 3, is intended to be immersed in a liquid wherein a collection is to be performed and a superstructure portion 4 forming the deck. The hull 2 and the superstructure 4 may be made, for example, of carbon fibers.

Figure 3:
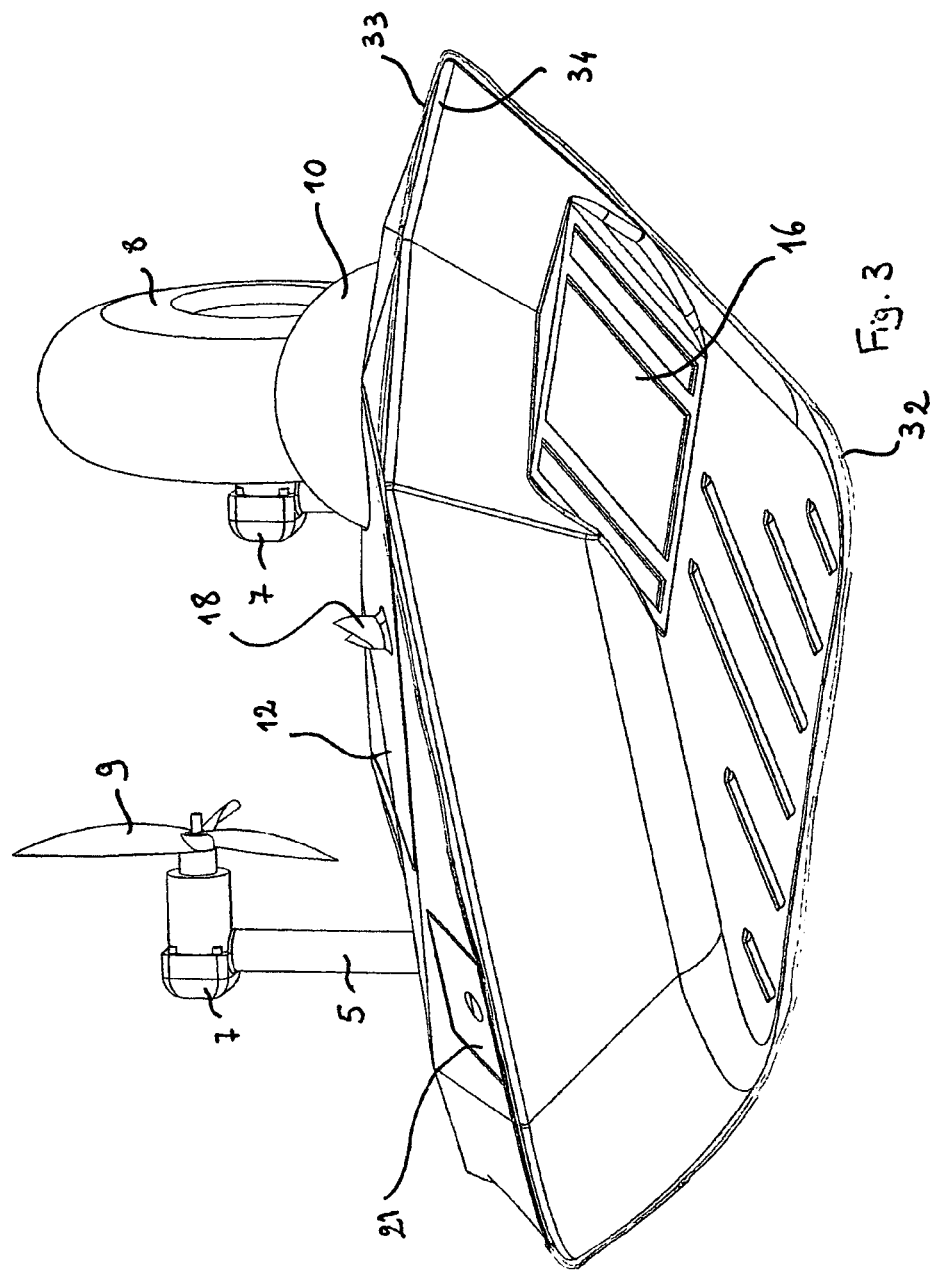
FIG. 3 is a three-quarter front perspective view of the immersed portion of the vessel.

FIG. 3 shows a major disposition of the invention where the canoe body 3 has no protruding portion. In other words, as can be seen in this figure, the canoe body 3 is devoid of any element or accessory forming an asperity, apart from two center-boards XX which contribute in maneuvering the vessel.

As will be seen later, this disposition is essential within the scope of the present invention.

Figure 2:
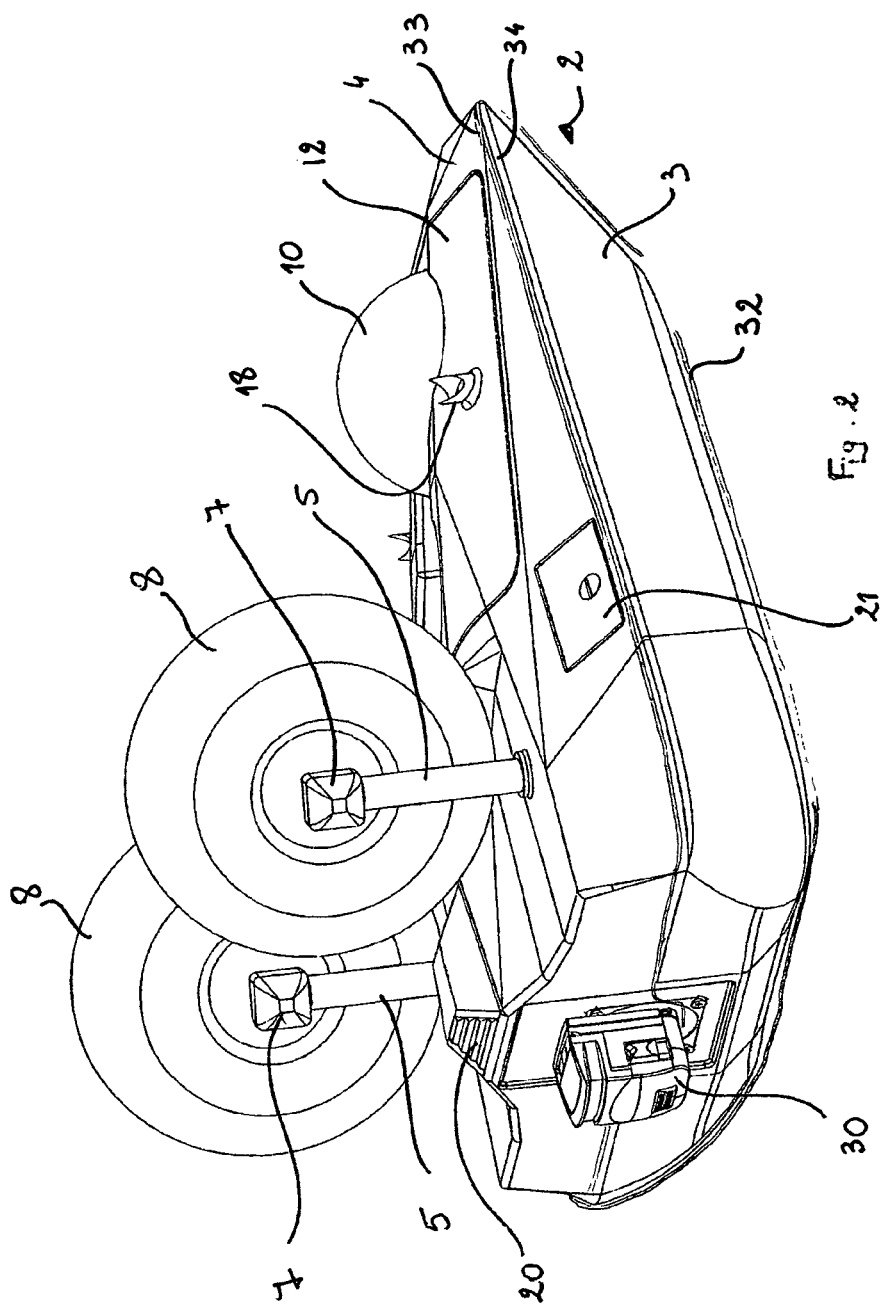
FIG. 2 is a three-quarter rear perspective view.

Referring to FIG. 2, it may be seen that the superstructure 4 has two masts 5 which, each, support an electric motor 7. The electric motor 7 disposed at the end of two masts drives a propeller 9. The propeller 9 is encapsulated in a cowling 8. The two propellers 9 are disposed on the rear portion of the deck.

The front portion of the deck is, in turn, fitted with two cells 10 which, in this instance, are disposed in tandem.

The two cells 10 are arranged in a removable cowl 12.

Figure 4:
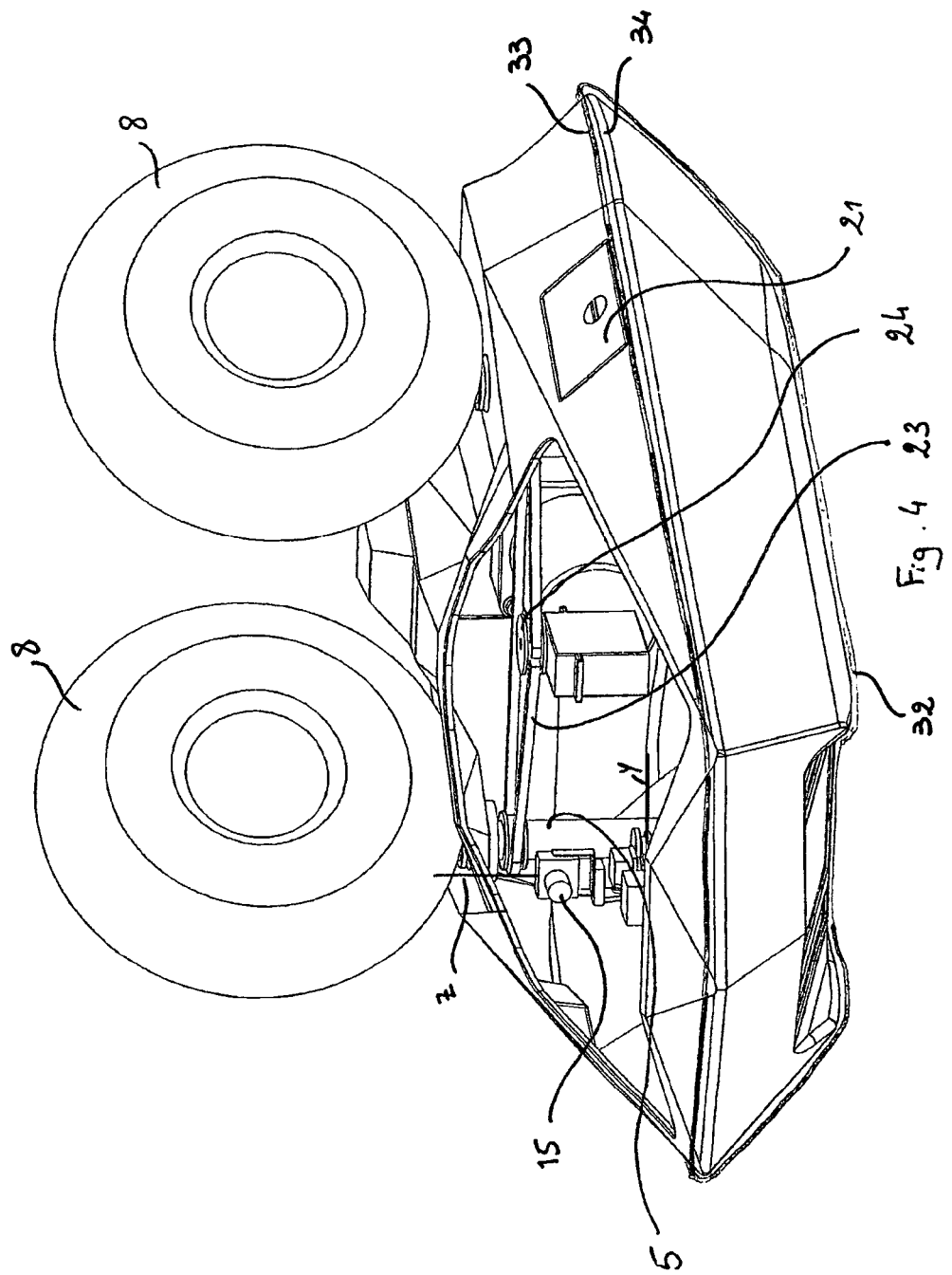
FIG. 4 is a view similar to FIG. 1 wherein a cowl is removed.

FIG. 4 shows the vessel in a configuration wherein the cowl 12 is removed.

The front cell 10 is fitted with a transparent bubble 13 and protects a camera 15. It may be seen that the camera 15 is disposed on an axis Z which allows it to rotate over a 360° angle.

The motion of the camera 15 is controlled by an electric motor.

It is specified that, in a variant of the invention, the panel 16 which is positioned at the stem area of the vessel may be transparent too. This disposition provides an underwater viewing area. This underwater viewing area may be utilized by tilting the camera so that instead of an aerial vision through the transparent bubble 13, the camera is positioned facing the transparent panel 16 of the stem area and provides an underwater vision.

In this embodiment, the camera 15 is movable along two axes. It is movable about a vertical axis so as to provide a vision up to 360° around the vessel and it is movable about a transverse axis Y so as to switch from an aerial position where the camera is positioned inside the transparent bubble 13 to an underwater position where the camera is facing the transparent panel 16.

The cell which is located behind the cell provided with the camera has a diameter allowing it to receive a container which is not represented in the figures.

It should also be noted the presence of the two side hatches 21.

The two masts 5 are connected to each other by a connecting member such as a belt 23 or a chain which is, itself, driven by a roller 24 or a toothed wheel connected to an electric motor.

Thus, when the motor connected to the roller 24 is actuated, each of the masts 5 and hence each of the propellers 9 rotates synchronously. This allows controlling the displacement of the vessel in the absence of an immersed rudder.

Although this does not appear in the figures, the inner cavity, which is delimited by the hull 2 and by the superstructure 4, receives the batteries which allow the powering of the different motors that have been described previously.

The two side windows 21 may be used to allow access to the batteries in order to recharge them. These batteries may be of the Lead technology, or Lithium-ion technology or Lithium-polymer technology.

In the example shown in FIGS. 1 to 4, it may also be seen that two air intakes 18 are disposed laterally on either side of the two cells. These two air intakes 18 act with an extractor 20 located at the rear portion of the vessel. This results in an air stream which allows ensuring extraction of the heat generated by the batteries and the electric motor.

FIG. 3 also shows one of the major elements of the invention which is the presence of a pump 30 fixed on the front portion of the vessel. Preferably, the pump is a peristaltic-type pump 30. The peristaltic pump 30, which comprises a roller assembly pressing an elastic tube is located outside the hull 2. A tube connected to the pump 30 plunges into the aquatic environment and supplies a collection container positioned in the aquatic vessel.

It is also provided control electronics which control all the aforementioned motors. In a manner known per se, the control electronics comprise means for wireless communication with a remote terminal which allows acting remotely on all the equipment embedded in the vessel, that is to say the motors, the pump, the camera as well as the motor or motors which control the displacement thereof.

One of the major points of the invention is the presence of a secondary hull 32 which fits over the hull 2 of the vessel.

Preferably, this secondary hull 32 is made of a plastic material and it has a peripheral fold-back 33 which allows it to snap-fit over a rib 34 formed in the illustrated case by the connecting edge between the hull 2 and the superstructure 4.

The secondary hull 32 is fitted by bending it so that it deviates and snap-fits over the rib 34 of the hull. For this purpose, the secondary hull 32 is fitted with a peripheral fold-back 35 which ensures the snap-fitting with the rib 34.

Thus, before a collection campaign is started, a secondary hull 32, which has sterility conditions, is fitted over the vessel. The vessel may then be launched into the water in the environment in question. The propellers 9 allow steering the vessel on the water plane.

The presence of the camera 15 contributes in piloting the vessel, when the vessel is no longer within the sight of the operator.

Once the collection campaign is performed, the vessel is removed from the water plane. The secondary hull 32 is removed from the vessel and depending on the case, it is withdrawn, recycled or sterilized.

The elastic tubes, which have allowed carrying out the collections, are also removed from the vessel in order to be withdrawn, recycled our sterilized, in the same manner.

The container in which the collected liquid sample is stored is removed from the vessel for analysis.

Moreover, the use of a peristaltic pump 30 allows guaranteeing, that no exchange with the inner portions of the vessel takes place.

It is specified that the vessel allows performing two types of collections. On the one hand, the vessel allows performing collections of liquids in a container; on the other hand, the vessel may be equipped with a filter capsule disposed downstream of the pump. In this last case, the filtrates are collected for analysis.

Hence, the invention provides a solution for carrying out collections in an aquatic environment in a fully sterile manner, since the vessel is provided with a single-use secondary hull, which guarantees the absence of any contamination of the environment.

Of course, the invention is not limited to the embodiment described above, but it encompasses all embodiments. Thus, instead of two synchronous propellers, it may be considered, in the case of a vessel of smaller size, to fit this latter with one single fixed aerial propeller with a rudder in tandem, this rudder is motorized and remote controlled. It may also be considered to fit the vessel with several pumps and/or several cells allowing to receive several containers where several collected samples may be stored.

Furthermore, the secondary hull may also be fixed over the hull of the vessel by fastening means such as screws/bolts, magnetic inserts, textile areas with loops and hooks.

The invention claimed is:

1. A floating vessel for collecting liquid samples comprising a hull having a canoe body intended to be immersed in a liquid environment below a waterline and a superstructure located above the waterline, the vessel comprising aerial propulsion means and means for collecting and storing samples and remote control means of the aerial propulsion means and collection means, the vessel further comprising a removable secondary hull fitted with means for fixing on the hull of the vessel covering at least the canoe body of the vessel.

2. The floating vessel according to claim 1, wherein the hull has a peripheral rib and the secondary hull (32) has a peripheral fold-back designed to snap-fit over the rib of the hull.

3. The floating vessel according to claim 1, wherein the vessel comprises a peristaltic pump comprising a roller assembly pressing an elastic tube located outside the hull.

4. The floating vessel according to claim 1, wherein the superstructure has a removable cowl wherein there is arranged at least one cell designed to receive a container wherein a collected sample may be stored.

5. The floating vessel according to claim 4, wherein the cowl comprises a transparent bubble located above a cell.

6. The floating vessel according to claim 1, wherein the vessel comprises at least one camera motorized with respect to at least one vertical axis Z of the vessel.

7. The floating vessel according to claim 5, wherein a camera is positioned in line with the transparent bubble.

8. The floating vessel according to claim 1, wherein the hull has, at the stem thereof, a transparent panel.

9. The floating vessel according to claim 6, wherein the camera is movable and is motorized about a transverse axis Y of the vessel so as to pivot from a position where the camera is positioned facing a transparent bubble and a position where the camera is positioned facing the transparent panel.

10. The floating vessel according to claim 1, wherein the secondary hull is made of a transparent material.

11. The floating vessel according to claim 1, wherein the vessel comprises at least one propeller positioned at the end of a mast projecting from the superstructure of the vessel, the propeller being driven by an electric motor placed at the top of the mast.

12. The floating vessel according to claim 11, wherein the vessel comprises two masts connected to each other by a drive belt allowing synchronizing the orientation of propellers.

13. The floating vessel according to claim 1, wherein the vessel embeds one or several batteries powering motors driving at least one of a pump, camera(s), and propeller(s).

* * * * *